United States Patent [19]

Sanford

[11] Patent Number: 4,568,647
[45] Date of Patent: Feb. 4, 1986

[54] METHOD AND ELEMENT FOR ALBUMIN ASSAY

[75] Inventor: Karl J. Sanford, Rochester, N.Y.

[73] Assignee: Eastman Kodak Company, Rochester, N.Y.

[21] Appl. No.: 540,975

[22] Filed: Oct. 11, 1983

[51] Int. Cl.[4] .................. G01N 21/78; G01N 33/68
[52] U.S. Cl. ........................................ 436/88; 422/56
[58] Field of Search .................. 436/86, 87, 169, 170, 436/88; 422/55, 56, 57, 58

[56] References Cited

U.S. PATENT DOCUMENTS

| | | | |
|---|---|---|---|
| 2,241,238 | 5/1941 | Brooker et al. | 430/591 |
| 2,553,206 | 12/1950 | Dent, Jr. et al. | 260/240.2 |
| 2,897,058 | 7/1959 | Galat | 436/87 |
| 3,359,072 | 12/1967 | Rey et al. | |
| 3,485,587 | 12/1969 | Keston | |
| 3,672,845 | 6/1972 | Verbeck | |
| 4,013,416 | 3/1977 | Rittersdorf et al. | |
| 4,230,456 | 10/1980 | Wu | |

FOREIGN PATENT DOCUMENTS 1177429 1/1970 United Kingdom .
1278621 6/1972 United Kingdom .

OTHER PUBLICATIONS

Nikolajewski et al., Chemical Abstracts, vol. 93, 1980, p. 214, No. 93:90449a.
Brooker et al., J.A.C.S., 73, p. 5332 (1951).
Sturmer et al., "The Theory of the Photographic Process", James (ed.), MacMillian Pub. Co., N.Y., 1977, pp. 194-196.
R. H. Henry et al., Clinical Chemistry Principles & Technics, pp. 449-451, Harper & Row, 1974.
Gustaffson, Clin. Chem., 22(5), pp. 616-622 (1976).
Webster, Clin. Chim. Acta, 53, pp. 109-115 (1974).

Primary Examiner—Arnold Turk
Attorney, Agent, or Firm—J. Lanny Tucker

[57] ABSTRACT

Disclosed herein is an assay for determination of albumin in a liquid sample. This assay involves the use of a dye of the structure:

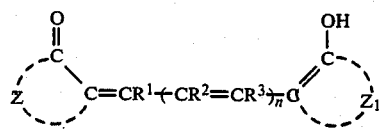

wherein n is zero or a positive integer up to 3; $R^1$, $R^2$ and $R^3$ are independently hydrogen, alkyl, cycloalkyl, aryl, alkoxy, aroxy, hydroxy, carboxy, alkoxycarbonyl, amino or a nonaromatic heterocyclic group; and Z and $Z_1$ independently represent the carbon, nitrogen, oxygen or sulfur atoms needed to complete a substituted or unsubstituted 5- to 7-membered carbocyclic or heterocyclic ring. This dye has a high affinity for albumin over a wide pH range. When the dye is bound to albumin, a shift in the dye spectral absorption occurs. Analytical elements containing this dye and an assay method are disclosed herein.

17 Claims, 2 Drawing Figures

METHOD AND ELEMENT FOR ALBUMIN ASSAY

FIELD OF THE INVENTION

The present invention relates to an assay for albumin. In particular, it relates to a method of detecting and quantifying albumin in biological and other liquids and to analytical elements useful in such method.

BACKGROUND OF THE INVENTION

Albumin is the smallest and most abundant of plasma proteins, generally having a molecular weight of about 69,000 and constituting slightly over half of the total protein in mammalian plasma. It is synthesized in the liver and has a half-life of about four weeks. In the human body, albumin has two important roles: (a) regulating the water balance between blood and tissues; and (b) functioning as a transport molecule for various materials which are only slightly soluble in water, such as bilirubin, fatty acids, cortisol, thyroxine and any number of drugs including sulfonamides and barbiturates.

It is frequently important to determine whether patients have a deficiency of serum albumin. Patients having such a deficiency suffer from edema which is characterized by an abnormal accumulation of serous fluid. Further, albumin deficiency can limit the transport of the slightly soluble materials noted above throughout the body.

Many methods, based on a variety of principles, have been described for the measurement of serum albumin. Of these, the methods based on dye-binding techniques are especially popular because they are readily automated and provide reproducible results. Most dye-binding techniques utilize pH indicator dyes which, on binding to a protein such as albumin, undergo a color transition characteristic of the change in pH while the solution pH is maintained constant with a buffer. Representative indicator dyes which exhibit these effects are methyl orange, bromocresol purple, bromophenol blue and bromocresol green.

However, it is known in the clinical chemistry art that such indicator dyes are not exclusively specific in binding to albumin. Rather, a number of other proteins found in the body, e.g. globulins, also bind to the indicator dyes and cause a color transition. Hence, assays utilizing indicator dyes tend to be inaccurate because they are not specific enough to albumin and are highly susceptible to binding with those so-called "interfering" proteins.

Indicator dyes are useful only in narrow pH ranges. Outside those ranges, the dyes either fail to change color upon binding to protein or change color prematurely. Further, albumin assays utilizing such indicator dyes are generally carried out at relatively low pH (e.g. at about 4.0 when using bromocresol green; at about 5.2 when using bromocresol purple) in order to increase the binding of dye to albumin and to allow for a color change in the dye absorption spectrum as a result of a pKa shift. However, since the pH transitions of the more commonly used dyes, e.g. bromocresol green and bromocresol purple are at acidic pH values, non-specific binding of those dyes with protein molecules other than albumin is increased. This undesirable effect is due to the fact that most proteins are positively-charged at acidic pH values whereas the dye molecules are negatively charged. At higher pH values, most proteins are negatively charged and non-specific ionic interactions are reduced.

Hence, there is a need in the art for an assay for albumin which is highly specific for that protein and which is useful over a relatively broad pH range and particularly at alkaline pHs.

SUMMARY OF THE INVENTION

The novel method and analytical elements of this invention provide an assay for albumin which is highly specific for albumin over other proteins often found in biological fluids. This assay can be used over a relatively broad pH range and particularly at alkaline pHs, thereby avoiding potential assay interference which can occur at lower pH. The assay of this invention utilizes a particular dye which is highly selective for albumin and when bound to albumin, exhibits a detectable shift in spectral absorption. The absorbance at the new $\lambda_{max}$ (absorption peak) can be correlated to the amount of albumin so that albumin can be quantified in an unknown sample.

In accordance with this invention, an analytical element for the determination of albumin in a liquid sample comprises a dye having the structure:

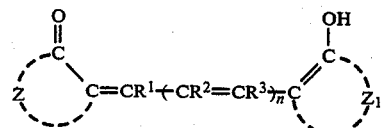

wherein n is zero or a positive integer up to 3; $R^1$, $R^2$ and $R^3$ are independently hydrogen, alkyl, cycloalkyl, aryl, alkoxy, aryloxy, hydroxy, carboxy, alkoxycarbonyl, amino or a nonaromatic heterocyclic group; and Z and $Z_1$ independently represent the carbon, nitrogen, oxygen or sulfur atoms needed to complete a 5- to 7-membered substituted or unsubstituted carboxylic or heterocyclic ring.

This invention further comprises a method for the determination of albumin in an aqueous liquid. This method comprises physically contacting a sample of the liquid with the dye described hereinabove to produce a shift in the $\lambda_{max}$ of the dye, and detecting the absorbance at that shifted $\lambda_{max}$.

DETAILED DESCRIPTION OF THE INVENTION

Figures 1, 2:
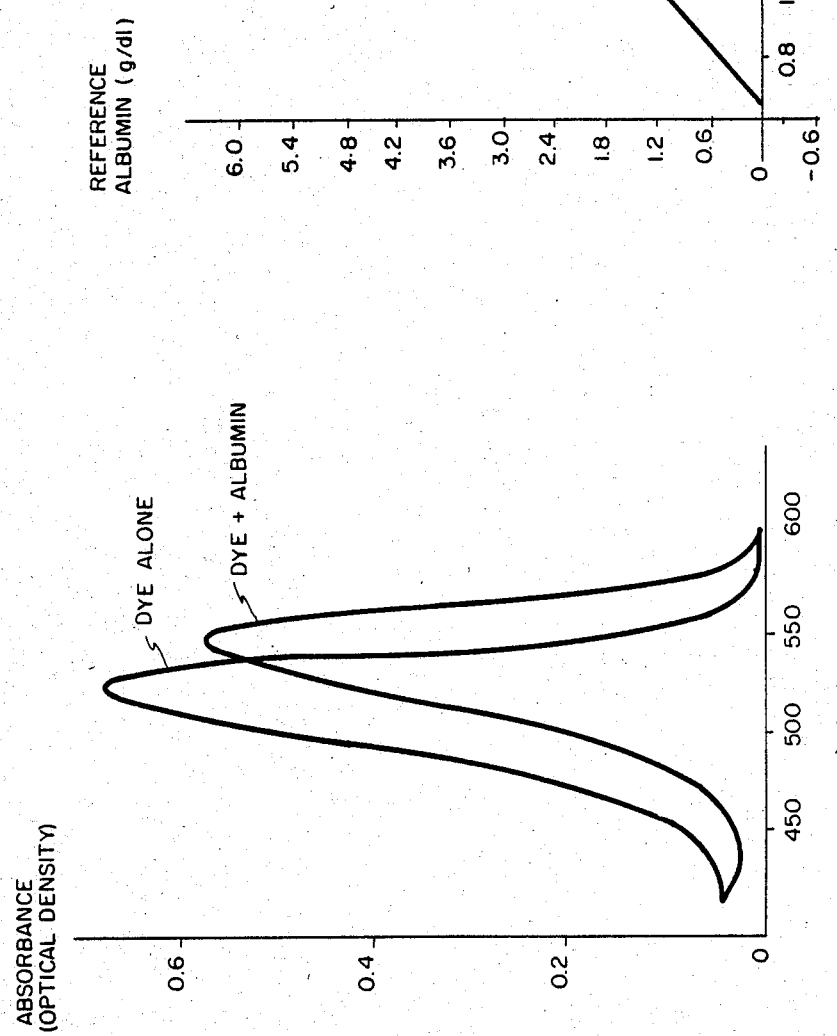
FIG. 1 is a graphical plot of absorbance versus spectral wavelength, illustrating the shift in spectral absorption exhibited by a composition of this invention in the presence of albumin.
FIG. 2 is a graphical plot of albumin concentration versus absorbance thereby providing a calibration curve for albumin.

The present invention relates to the detection and quantification of the albumin in aqueous liquids. The practice of this invention can be accomplished with biological fluids, e.g. whole blood, plasma, sera, lymph, bile, urine, spinal fluid, sputum, sweat and the like as well as stool secretions of humans or animals. It is also possible to use fluid preparations of human or animal tissue such as skeletal muscle, heart, kidney, lungs, liver, brains, bone marrow, skin and the like. The preferred biological fluid for practice of this invention is human blood serum.

The dyes useful in the practice of this invention are those having the structure:

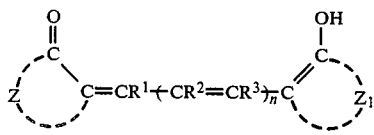

or equivalent alkali metal or ammonium salts (including pyridinium) thereof, wherein n is zero or a positive integer up to 3, and preferably n is 1 or 2; $R^1$, $R^2$ and $R^3$ are independently hydrogen, alkyl, preferably of 1 to 10 carbon atoms (e.g. substituted or unsubstituted methyl, ethyl, propyl, and isomers thereof, benzyl, chloromethyl, etc.); cycloalkyl, preferably of 4 to 12 carbon atoms (e.g. substituted or unsubstituted cyclobutyl, cyclopentyl, cyclohexyl, etc.); aryl, preferably of 6 to 18 carbon, nitrogen, oxygen or sulfur atoms in the ring (e.g. substituted or unsubstituted, carbocyclic or heterocyclic, such as phenyl, naphthyl, xylyl, pyridyl, etc.); alkoxy, preferably of 1 to 10 carbon atoms (e.g. substituted or unsubstituted methoxy, chloromethoxy, ethoxy, propoxy, benzoxy, etc. and isomers thereof); aryloxy, preferably of 6 to 18 carbon, nitrogen, oxygen or sulfur atoms in the ring (e.g. substituted or unsubstituted phenoxy, etc.); hydroxy; carboxy, or equivalent alkali metal or ammonium salts; alkoxycarbonyl, preferably of 2 to 12 carbon atoms (e.g. substituted or unsubstituted methoxycarbonyl, ethoxycarbonyl, etc. and isomers thereof); amino (including mono- and diamino, e.g. anilyl); or a nonaromatic heterocyclic group, preferably of 5 to 12 carbon atoms (e.g. substituted or unsubstituted piperyl, tetrahydropyranyl, etc.). Preferably, $R^1$, $R^2$, and $R^3$ are independently hydrogen, alkyl or aryl as defined hereinabove.

Z and $Z_1$ independently represent the carbon, nitrogen, oxygen or sulfur atoms needed to complete a 5- to 7-membered substituted or unsubstituted carbocyclic or heterocyclic ring. In other words, Z and $Z_1$ can be the same or different. The rings can be aromatic or nonaromatic. Preferably, Z and $Z_1$ represent only carbon and nitrogen atoms. More preferably, Z and $Z_1$ independently represent the carbon or nitrogen atoms needed to complete a 5- to 6-membered substituted or unsubstituted heterocyclic ring. These cyclic rings can be independently substituted with one or more of the groups described hereinabove for $R^1$, $R^2$ and $R^3$ as well as oxo and thioxo groups. Preferably, each ring is substituted with at least one phenyl group which in turn has a carboxy or sulfo substituent.

Examples of dyes useful in the practice of this invention are as follows, with the dye labeled I being a particularly useful one:

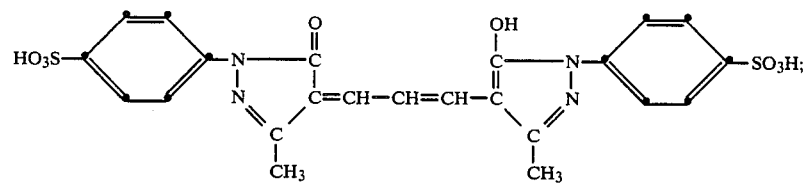

I.

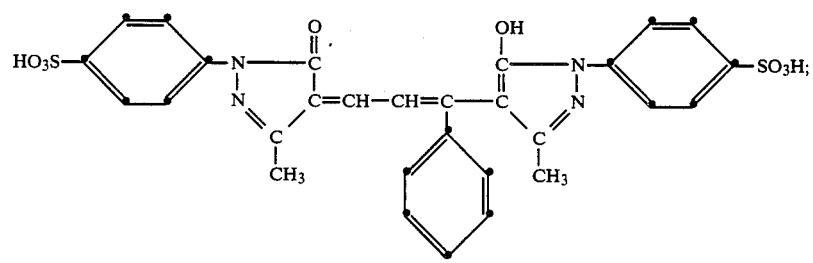

II.

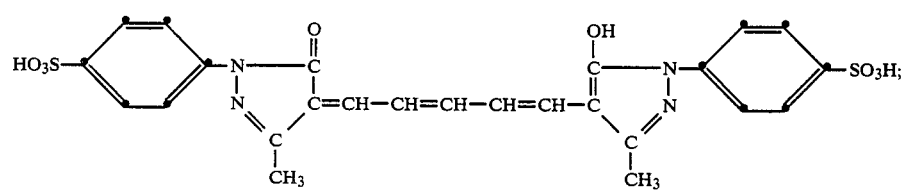

III.

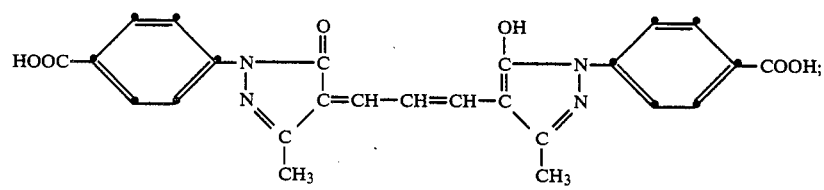

IV.

-continued
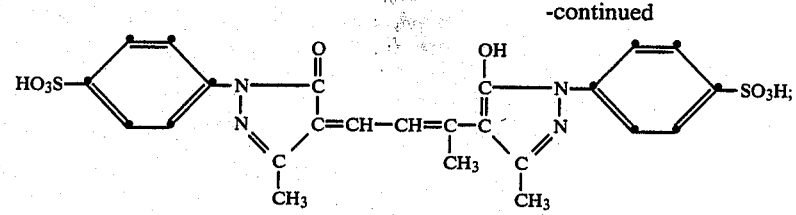 V.
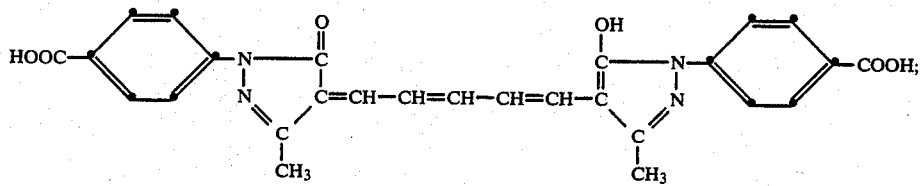 VI.
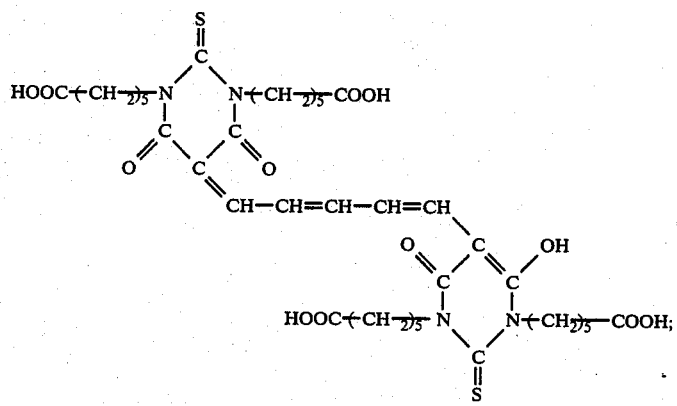 VII.
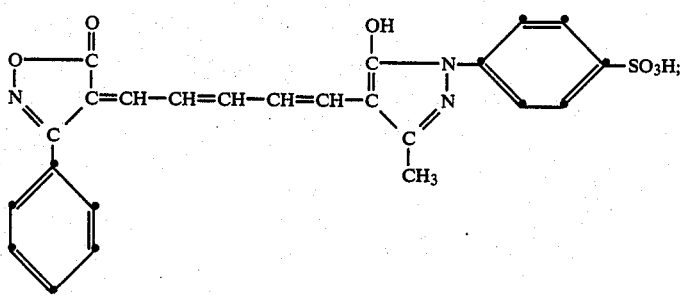 VIII.
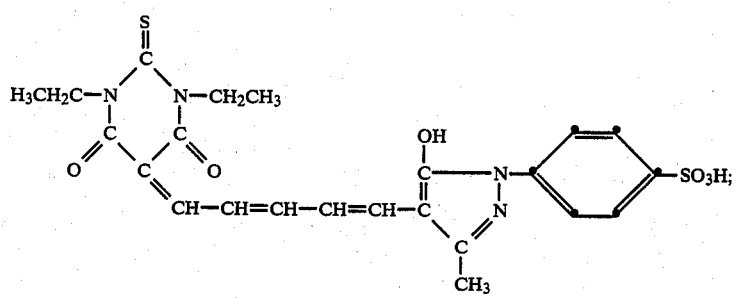 IX.
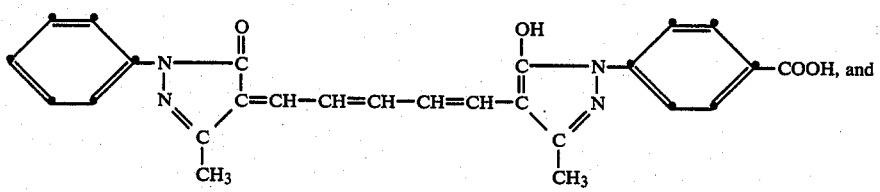 X.

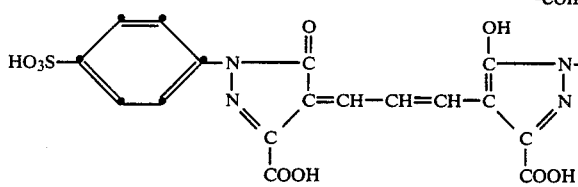 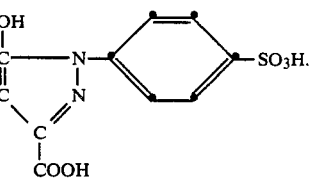

XI.

-continued

The dyes useful in the practice of this invention are either commercially available (e.g. from Eastman Kodak Company, Rochester, N.Y.), or can be readily prepared by a person of ordinary skill in the art.

The assay of this invention is preferably, although not necessarily, carried out at a pH within the range of from about 5 to about 11, and preferably within the range of from about 6 to about 11. This is a relatively broad pH range for an albumin assay because the known albumin assays are limited to quite narrow pH ranges in order to utilize indicator dyes. In the practice of the present invention, the desired pH can be maintained with any suitable buffer (see, e.g. H. E. Good et al, *Biochem.*, 5(2), pp. 467–477, 1966). Useful buffers include phosphates, borates, acetates, etc. with the borates being preferred. Examples of other buffers are well known in the art. When used in the elements described hereinbelow, the buffer is selected to provide a pH within the range of from about 5 to about 11, and preferably from about 6 to about 11, under conditions of use (i.e. when wetted with an aqueous liquid sample).

This invention can be practiced by first preparing an aqueous solution of a dye described hereinabove with a suitable buffer. The final concentration of the dye should be low enough to minimize the effect of potential interferents in the test liquid, but high enough to provide reliable quantitative results. Generally, the final dye concentration is within the range of from about $10^{-4}$ to about $10^{-6}$M, and preferably within the range of from about $1 \times 10^{-5}$ to about $4 \times 10^{-5}$M. From about 2 to about 20 mg of the dye is generally mixed with from about 100 to about 2000 mL of buffer.

The method of this invention is adaptable to both solution and dry element albumin assays. Thus, in a solution assay, a sample of the dye (with or without buffer) is placed in a spectrophotometer to determine the absorption spectrum. A liquid suspected of containing albumin is then added to the dye sample and the spectral absorption is monitored again to determine if a spectral shift has occurred. The optical density of the new (or shifted) $\lambda_{max}$ (absorption peak) is then compared to a predetermined calibration curve to predict the amount of albumin in the liquid sample. This solution assay procedure is described in more detail in Examples 1 and 2 hereinbelow.

Alternatively, the dye described hereinabove is included in a dry analytical element, such as one described in U.S. Pat. Nos. 3,992,158 (issued Nov. 16, 1976 to Przybylowicz et al); 4,042,335 (issued Aug. 16, 1977 to Clément); and 4,258,001 (issued Mar. 24, 1981 to Pierce et al), the disclosures of which are incorporated herein by reference. The presence and amount of albumin is determined by physically contacting the element with the liquid sample suspected of containing albumin. Such contacting can be, for example, by spotting or dispensing by hand or machine from a suitable dispensing means. Alternatively, the element is dipped or immersed into the liquid sample. The spectral absorption of the dye in the element is measured both before and after contact with the liquid sample and any shift in spectral absorption is evaluated to determine the presence and amount of albumin in the liquid.

The elements of this invention are self-supporting or carried on a support. Useful support materials include a variety of polymeric materials, such as cellulose acetate; polyesters, e.g. poly(ethylene terephthalate); polycarbonates; and polyvinyl compounds, such as polystyrenes, etc. Preferred supports include radiation-transmissive (i.e. substantially transparent) support materials that transmit electromagnetic radiation of a wavelength within the region between about 200 and 900 nm, as well as radiation due to radioactivity.

The elements generally comprise a support having thereon, in order and in fluid contact, a reagent zone and a spreading zone although the element can contain, if desired, a single spreading/reagent zone. The term "fluid contact" means that fluids can pass between superposed regions of adjacent zones. States in another manner, "fluid contact" refers to the ability to transport components of a fluid between the zones in fluid contact. Preferably, each zone is a separate coated layer, although one or more zones can be in a single layer of an element. Typical dry element formats and materials are known in the art and described, for example, in U.S. Pat. Nos. 3,992,158, noted hereinabove; 4,042,335, noted hereinabove; 4,144,306 (issued Mar. 13, 1979 to Figureas); 4,132,528 (issued Jan. 2, 1979 to Eikenberry et al); 4,050,898, noted hereinabove; 4,258,001, noted hereinabove and 4,333,733 (issued June 8, 1982 to Sanford et al). The elements can contain one or more interlayers or subbing layers comprised of appropriate materials.

One or more zones of the elements of this invention can contain a variety of other desirable, but optional, components, including surfactants, binders (generally hydrophilic natural or synthetic colloids or polymers), solvents, etc as known in the art.

The spreading zone is generally a layer that accepts a liquid sample, whether applied directly to the layer or provided to it from a layer or layers in fluid contact with the spreading layer, and within which the solvent or dispersion medium of the sample and albumin is distributed such that a uniform apparent concentration of albumin is provided at the surface of the spreading layer facing the reagent layer of the element. useful spreading zones are described, for example, in U.S. Pat. Nos. 3,992,158 and 4,258,001, both noted hereinabove; and U.K. Patent Application No. 2,052,057 (published Jan. 21, 1981). The spreading zones can be composed of either fibrous or non-fibrous materials, or both.

The coverage of the reagents (i.e. dye and buffer) in the element can be within a broad range depending upon the liquid to be assayed. For example, the dye is generally present in a coverage of from about 0.01 to about 3 g/m², and preferably from about 0.03 to about 1 g/m². The optional buffer is generally present in a coverage of from about 0.1 to about 10 g/m², and preferably from about 0.5 to about 6 g/m².

A variety of different elements, depending on the method of analysis, can be prepared in accordance with the present invention. Elements can be configured in a variety of forms, including elongated tapes of any desired width, sheets or smaller chips.

In an analytical method using these elements, which method could be manual or automated, the element is taken from a supply roll, chip packet or other source and positioned to receive a free drop, contact spot or other form of liquid sample, such as from an appropriate dispenser. After sample application, the element is exposed to any conditioning, such as incubation, heating or the like, that may be desirable to quicken or otherwise facilitate obtaining any test result.

The dye is then allowed to react with any albumin in the liquid sample and the spectral absorption is measured by passing the element through a zone in which suitable apparatus for reflection or transmission spectrophotometry is provided.

The following examples illustrate the practice of the invention. In these examples, the human transferrin was obtained as a 90% pure preparation from Sigma Chemical Co., St. Louis, Mo. Human alpha, beta and gamma globulins and bovine gamma globulin were obtained from Miles Laboratories, Inc., Elkhart, Ind. and used without further purification. The dyes and buffers were obtained from Eastman Kodak Company, Rochester, N.Y. Unless otherwise specified, all chemicals used were reagent grade. All biochemicals were stored at 4° C. until used.

Albumin calibrators were gravimetrically prepared from human serum albumin (Miles Pentex Fraction V) in Ringer's Solution (isotonic solution composed of 0.9% NaCl, 0.033% $CaCl_2$ and 0.03% KCl). Calibrator levels were assigned using the ten-second bromocresol green method (see Gustafson, *Clin. Chim.*, 22(5), pp. 616–622, 1976). Human sera were obtained from local hospitals. Samples not immediately used were kept frozen at −80° C. Calibrators prepared from pooled human serum samples were diluted with Ringer's Solution to achieve additional levels and were determined as described above.

EXAMPLE 1

Solution Assay of Albumin

A $1.48 \times 10^{-5}$M dye solution comprising Dye I noted hereinabove was prepared in 50 mM phosphate buffer (pH 8.1). A sample of this solution was placed in a cuvette and the absorption spectrum (400–600 nm) was recorded on a conventional spectrophotometer. A small amount of human serum albumin ($1.5 \times 10^{-5}$M) was then added to the dye solution and the absorption spectrum again recorded. As shown in FIG. 1, the dye solution without albumin displayed a narrow spectrum with an apparent absorbance maximum at about 520 nm, whereas, in the presence of albumin, the absorbance maximum was shifted about 35 nm to about 555 nm.

EXAMPLE 2

Preparation of Calibration Curve for Albumin

Calibrators were formulated from pooled human serum as described hereinabove in concentrations of 1.29 g/dL, 2.11 g/dL, 3.04 g/dL and 4.79 g/dL. Each calibrator (0.015 mL) was added to a cuvette containing 1 mL of dye solution prepared as described in Example 1. Each cuvette was covered, gently shaken several times and placed in a conventional spectrophotometer. The phosphate buffer was used as a blank for each measurement. After 2 minutes, the absorbance at 565 nm was recorded for each sample. Using the absorbance data, the calibration curve of FIG. 2 was prepared having a slope of 8.1 and an intercept of $-1.7 \times 10^{-1}$. The curve is linear through about 5 g/dL.

EXAMPLE 3

Binding Specificity of Dye I for Albumin

The binding specificity of Dye I for various serum proteins, e.g. human albumin, alpha and beta globulins, and bovine gamma globulin was determined by observing the effect of the various proteins in the dye spectrum. Various amounts of 5% aqueous protein solutions were added to 1 mL of $3.12 \times 10^{-4}$M dye solution and referenced against the 50 mM phosphate buffer solution. Each resulting dye-protein solution was gently shaken during a 2 minute incubation period and its spectral absorbance was recorded at 565 nm as described hereinabove. The results shown in Table I hereinbelow illustrate the specificity of Dye I for albumin because of the change in absorbance of the dye relative to increasing amount of protein which occurred for albumin only. The other serum protein fractions did not cause a density change in the dye absorption spectrum.

TABLE I

| Protein Level (μL) | Absorbance | | | |
|---|---|---|---|---|
| | Human Albumin | Human Alpha Globulin | Human Beta Globulin | Bovine Gamma Globulin |
| 0 | 0.54 | 0.54 | 0.52 | 0.52 |
| 10 | 0.92 | 0.54 | 0.52 | 0.52 |
| 20 | 1.32 | NA | NA | NA |
| 40 | 1.76 | NA | NA | NA |
| 50 | NA | 0.54 | NA | 0.52 |
| 60 | 2.40 | NA | NA | NA |

NA = not available

EXAMPLE 4

Binding Specificity of Dyes II–VII for Albumin

The albumin binding specificity of Dyes II–VII, illustrated hereinabove, was evaluated in the following manner. 30 μL Aliquots of 5% protein solutions, including human albumin and alpha globulin, and bovine gamma globulin were added to 3 mL of dye solution and referenced against a phosphate buffer blank (10 μL and 15 μL aliquots of the protein solutions were added to 1 mL of solutions of Dyes III and VII, respectively). The dye concentrations are indicated in Table II hereinbelow. Each dye-protein solution was gently shaken during a 2 minute incubation period and its maximum absorbance ($\lambda_{max}$) was recorded as described hereinabove. The results shown in Table II indicate that Dyes II–VII are highly specific for albumin. The absorbances were measured at various wavelengths depending on the specific dye.

TABLE II

| Dye | Dye Concentration ($\times 10^{-5}$ M) | Wavelength ($\lambda$ max) | Blank Optical Density | Absorbance Change* | | |
|---|---|---|---|---|---|---|
| | | | | 5% Albumin | 5% Alpha Globulin | 5% Gamma Globulin |
| II | 1.16 | 575 | 0.12 | 0.110 | 0.020 | −0.020 |
| III | 1.68 | 650 | 0.000 | 0.856 | 0.135 | 0.013 |
| IV | 0.96 | 560 | 0.028 | 0.162 | 0.068 | 0.022 |
| V | 1.48 | 575 | 0.035 | 0.235 | 0.031 | 0.015 |
| VI | 3.67 | 650 | 0.120 | 0.387 | 0.080 | 0.010 |
| VII | 0.79 | 655 | 0.560 | 0.880 | 0.120 | 0.020 |

*Change = (protein optical density) - (blank optical density)

EXAMPLE 5

Comparison of Invention Assay to State-of-the-Art Assays

This is a comparative example comparing the protein sensitivity of the albumin assay of the present invention to the protein sensitivities of two state-of-the-art albumin assays.

Human alpha, beta and gamma globulins and transferrin (a component of gamma globulin) were added to individual pooled human serum samples to provide test samples which would be similar to the serum of a person suffering from abnormally low albumin levels (based on total protein). The resulting serum-protein solutions containing differing amounts of protein were assayed using the assay composition of Example 1. A DuPont aca (4.5 minute end point) assay and the 10-sec. bromocresol green assay were used as control assays (the latter is described in *Clin. Chem.*, 22(5), pp. 616–622 (1976)). The results of these assays, presented in Table III hereinbelow, indicate that the assay of this invention is generally insensitive to all of the shown interfering serum proteins at these concentrations. The control albumin assays are insensitive to some interferents but extremely sensitive to others.

TABLE III

| | ASSAY | | | | | |
|---|---|---|---|---|---|---|
| SOLUTION | aca (g/dl) | Change* (%) | Bromocresol Green (g/dl) | Change* (%) | Dye I Solution (g/dl) | Change* (%) |
| Serum | 4.66 | — | 3.95 | — | 3.91 | — |
| Serum + 3% α-globulin | 5.88 | 1.22 (26) | 4.61 | 0.66 (17) | 4.03 | 0.12 (3) |
| Serum + 3% β-globulin | 5.02 | 0.36 (8) | 4.39 | 0.44 (11) | 3.90 | 0.01 (0) |
| Serum + 3% γ-globulin | 4.77 | 0.11 (2) | 3.99 | 0.04 (1) | 3.93 | 0.02 (0) |
| Serum + 5% transferrin | 7.89 | 3.23 (69) | 3.95 | 0 (0) | 3.89 | 0.02 (0) |

*Change = deviation (g/dl) from serum solution having only albumin protein
(%) = percentage change from value of serum solution having only albumin protein

EXAMPLE 6 pH Effects on Albumin Determination

The effects of pH on the determination of albumin according to this invention were evaluated by observing the effect of pH on the absorbance of the albumin-dye complex at the Dye I $\lambda_{max}$ of 565 nm.

Dye solutions were prepared as described in Example 1 using $1.48 \times 10^{-5}$M Dye I in 50 mM of two different phosphate buffers (pH 6.3 and 8.1) and in 50 mM of borate buffer (pH 10).

Varying amount of a 5 g/dL stock solution of albumin, as shown in Table IV hereinbelow, were added to the dye solutions, and the resulting optical density (absrobance) of each sample was recorded using a conventional spectrophotometer. The results shown in Table IV indicate that there is little difference in absorbance at each pH. Hence, the assay of the present invention is useful over a broad pH range using the appropriate buffer.

TABLE IV

| Albumin Stock Solution (μL) | Absorbance (Optical Density) at $\lambda$ max 565 nm | | |
|---|---|---|---|
| | pH 6.3 | pH 8.1 | pH 10 |
| 0 | 0.031 | 0.025 | 0.030 |
| 5 | 0.255 | 0.170 | 0.180 |
| 10 | 0.340 | 0.250 | 0.260 |

EXAMPLE 7

Dry Analytical Element for Albumin Assay

This example illustrates how a dry analytical element for assay of albumin could be prepared and used in the practice of this invention. The element would have the following format and components:

| | |
|---|---|
| Spreading Layer | Poly(vinyltoluene-co-p-t-butyl-styrene-co-methacrylic acid) (61:37:2 weight ratio) beads (20–60μ in size) (150–170 g/m²) Poly(n-butyl acrylate-co-styrene-co-2-acrylamido-2-methylpropane sulfonic acid) (70:20:10 weight ratio) (5–20 g/m²) Zonyl FSN ™ surfactant* (0.2–2 g/m²) |
| Reagent Layer | Poly(acrylamide-co-N—vinyl-2-pyrrolidone) (50:50 weight ratio) (5–50 g/m²) Zonyl FSN ™ surfactant (0.2–2 g/m²) Dye I** (0.01 to 3 g/m²) Borate buffer (pH 10) (0.1–10 g/m²) |
| Poly(ethylene terephthalate) Support | |

*Commercially available from DuPont, Wilmington, Delaware.
**Described hereinabove.

The above-described analytical element could be used to determine albumin in a biological fluid, e.g. blood serum, in the following manner. A 10 μL aliquot sample of blood serum would be "spotted" (dispensed) onto the spreading layer of the element. Any albumin present in the sample would interact with Dye I and cause a shift in the dye's $\lambda_{max}$ (absorption maximum). The shift in $\lambda_{max}$ would then be determined with a conventional spectrophotometer, scanning for absorption between about 500 and 600 nm. Comparison to a calibrator curve would reveal the amount of albumin present in the sample, if any.

Although this invention has been described in detail with particular reference to preferred embodiments thereof, it will be understood that the variations and modifications can be effected within the spirit and scope of the invention.

I claim:

1. A method for the determination of albumin in an aqueous liquid, said method comprising the steps of:
   (1) physically contacting a sample of said liquid and a dye having the structure:

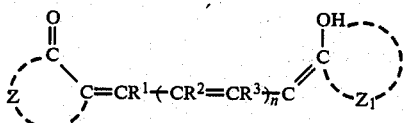

wherein n is zero or a positive integer up to 3; $R^1$, $R^2$ and $R^3$ are independently hydrogen, alkyl, cycloalkyl, aryl, alkoxy, aryloxy, hydroxy, carboxy, alkoxycarbonyl, amino or a nonaromatic heterocyclic group; and Z and $Z_1$ independently represent the carbon, nitrogen, oxygen or sulfur atoms needed to complete a 5- to 7-membered substituted or unsubstituted carbocyclic or heterocyclic ring, to produce a shift in the $\lambda_{max}$ of said dye; and
   (2) detecting the absorbance at said shifted $\lambda_{max}$.

2. The method of claim 1 wherein n is 1 or 2; $R^1$, $R^2$ and $R^3$ are independently hydrogen, alkyl or aryl; and Z and $Z_1$ independently represent the carbon, nitrogen, oxygen or sulfur atoms needed to complete a substituted or unsubstituted 5- or 6-membered heterocyclic ring.

3. The method of claim 1 wherein said sample-dye contacting is carried out in the presence of a buffer which provides a pH in the range of from about 5 to about 11.

4. The method of claim 2 wherein said dye is selected from the group consisting of:

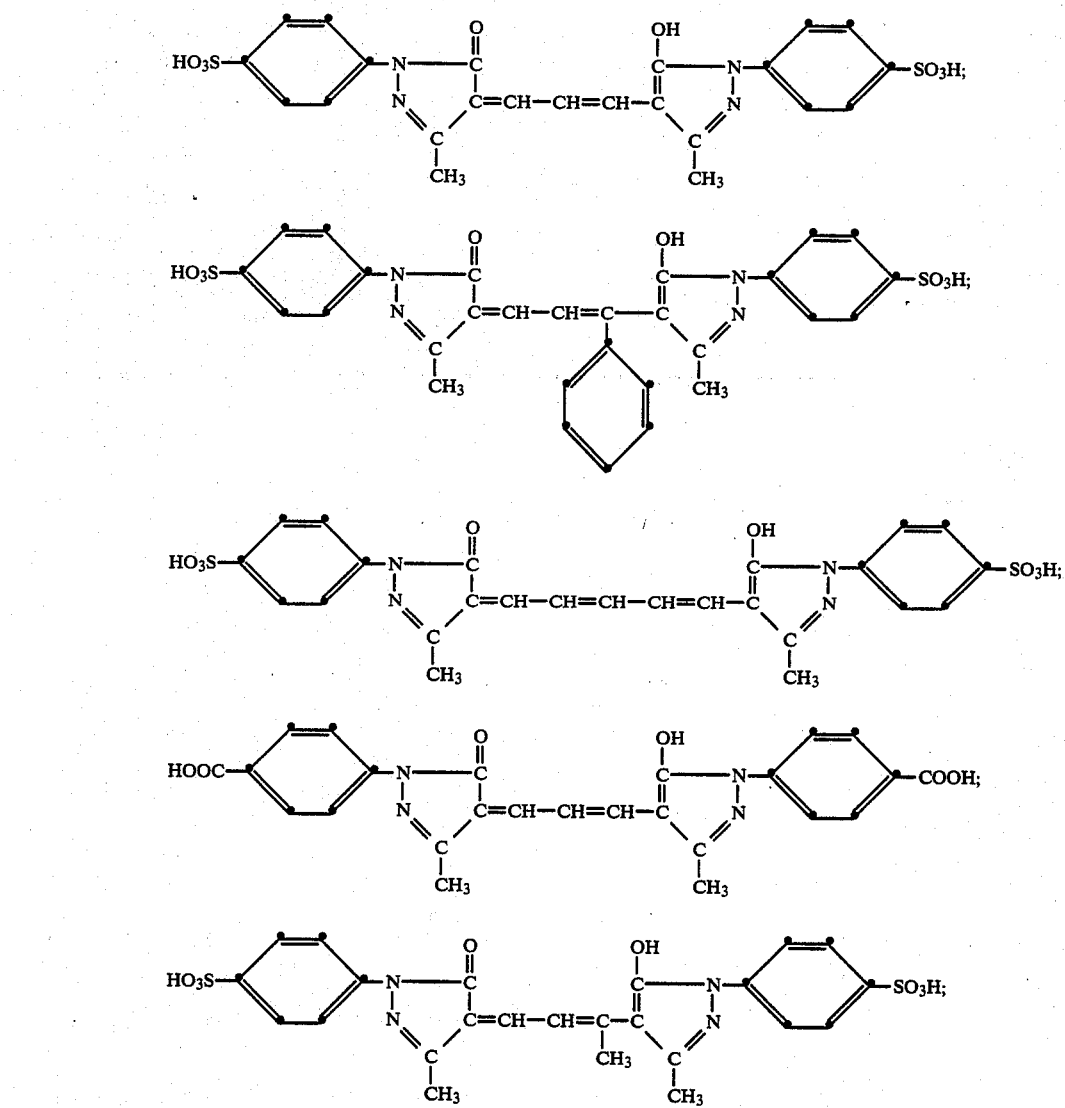

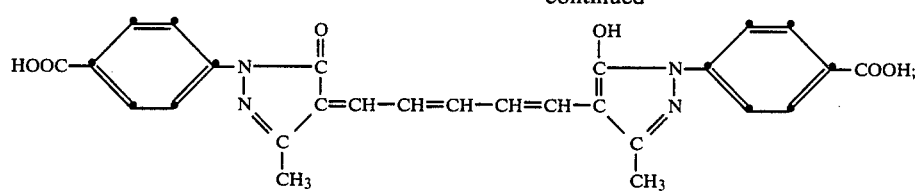
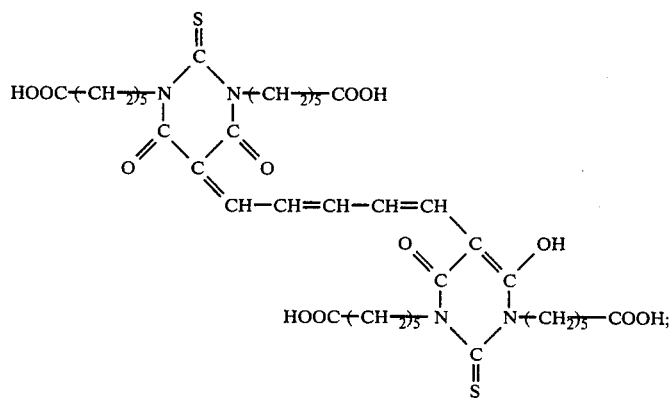
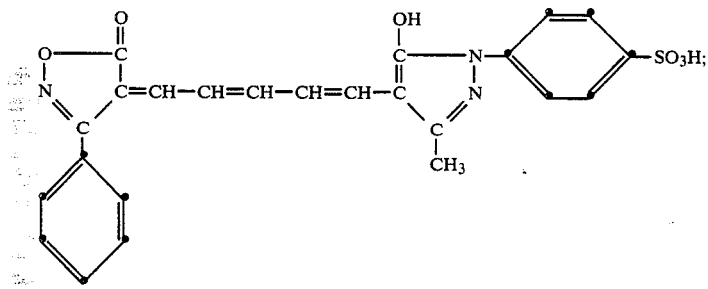
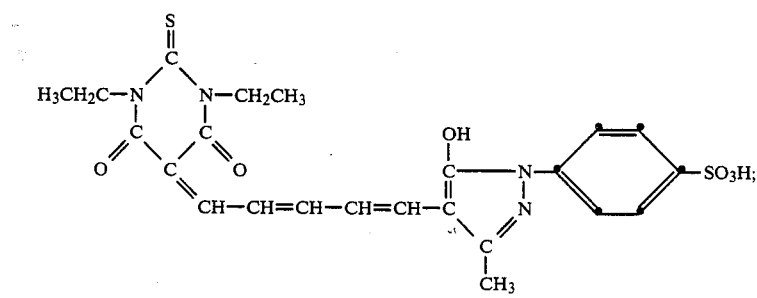
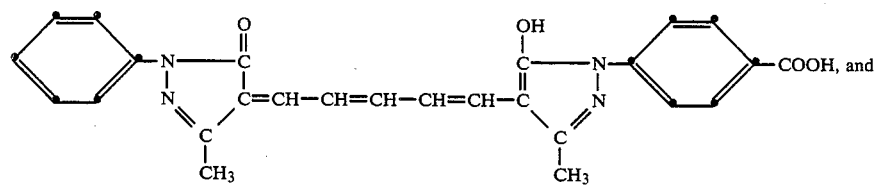
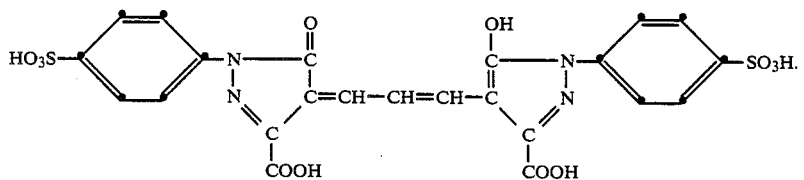
5. The method of claim 4 wherein said dye is:

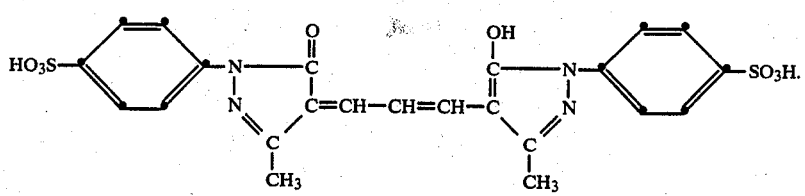

6. A method for the determination of albumin in an aqueous liquid, said method comprising the steps of:
   (1) physically contacting a sample of said liquid and an analytical element, said element comprising a support containing a dye having the structure:

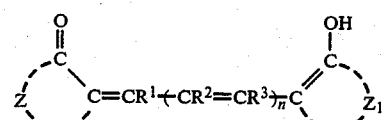

wherein n is zero or a positive integer up to 3; $R^1$, $R^2$ and $R^3$ are independently hydrogen, alkyl, cycloalkyl, aryl, alkoxy, aryloxy, hydroxy, carboxy, alkoxycarbonyl, amino or a nonaromatic heterocyclic group; and Z and $Z_1$ independently represent the carbon, nitrogen, oxygen or sulfur atoms needed to complete a substituted or unsubstituted 5- to 7-membered carbocyclic or heterocyclic ring to produce a shift in the $\lambda_{max}$ of said dye; and
   (2) detecting the absorbance at said shifted $\lambda_{max}$.

7. The method of claim 6 wherein said element comprises a support having thereon, in order and in fluid contact, a reagent zone and a spreading zone, said reagent zone containing said dye.

8. The method of claim 7 wherein said reagent zone comprises a buffer which provides a pH in the range of from about 6 to about 11 under conditions of use.

9. The method of claim 7 wherein said aqueous liquid is blood serum.

10. An analytical element for the determination of albumin in a liquid sample, said element comprising a support containing a dye having the structure:

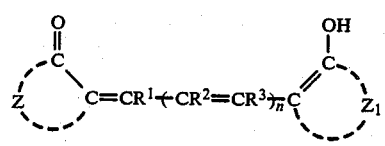

wherein n is zero or a positive integer up to 3; $R^1$, $R^2$ and $R^3$ are independently hydrogen, alkyl, cycloalkyl, aryl, alkoxy, aryloxy, hydroxy, carboxy, alkoxycarbonyl, amino or a nonaromatic heterocyclic group; and Z and $Z_1$ independently represent the carbon, nitrogen, oxygen or sulfur atoms needed to complete a 5- to 7-membered substituted or unsubstituted carbocyclic or heterocyclic ring, said dye being present at a coverage of from about 0.01 to about 3 $g/m^2$ and being capable of exhibiting a detachable shaft in spectral absorption when bound to albumin.

11. The element of claim 10 wherein n is 1 or 2; $R^1$, $R^2$ and $R^3$ are independently hydrogen, alkyl or aryl; and Z and $Z_1$ independently represent the carbon, nitrogen, oxygen or sulfur atoms needed to complete a substituted or unsubstituted 5- or 6-membered heterocyclic ring.

12. The element of claim 11 wherein said dye is selected from the group consisting of:

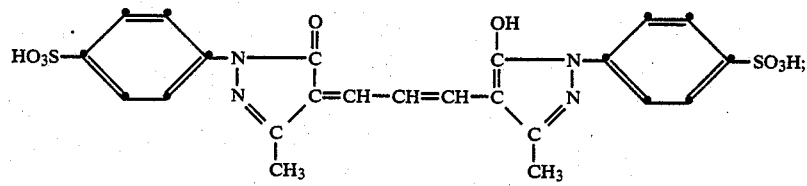

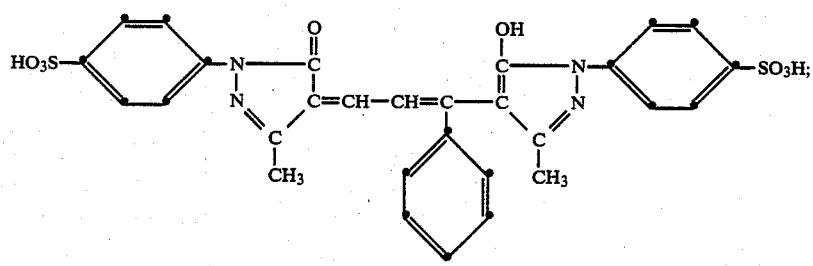

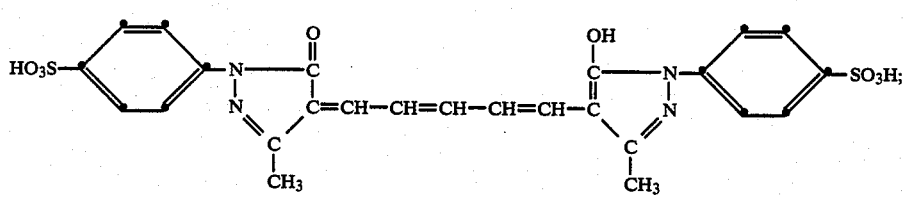

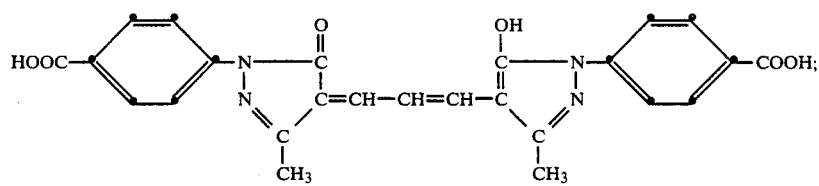
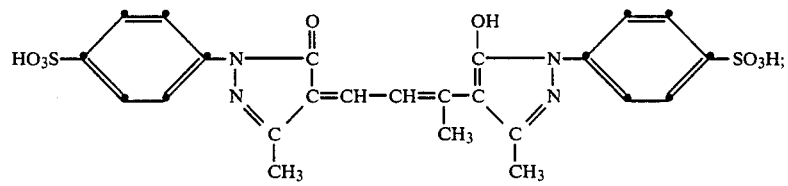
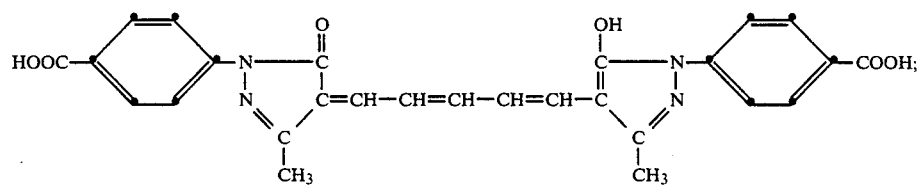
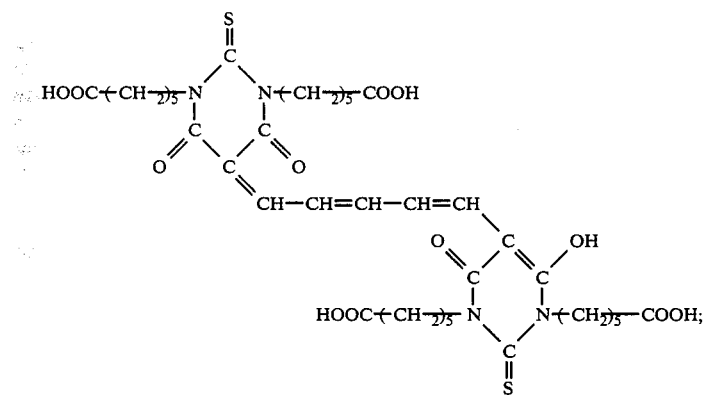
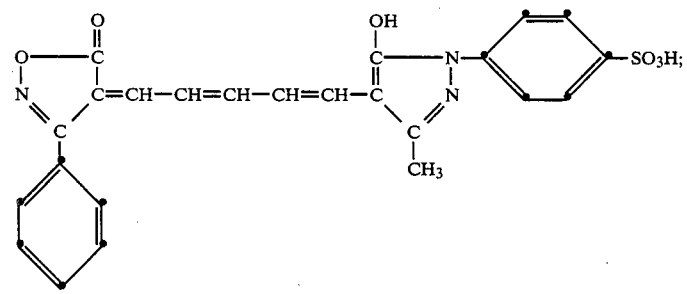
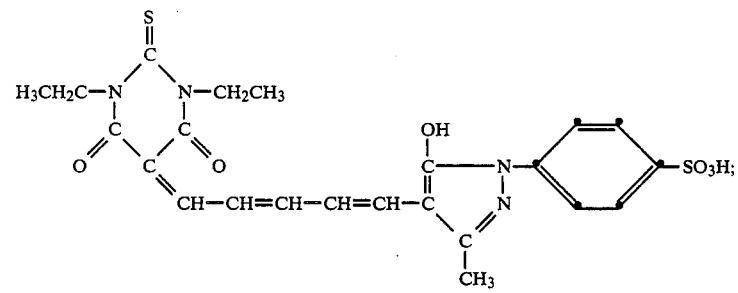

-continued

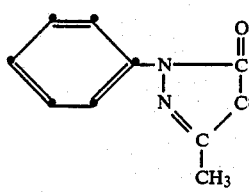 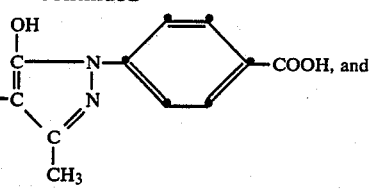

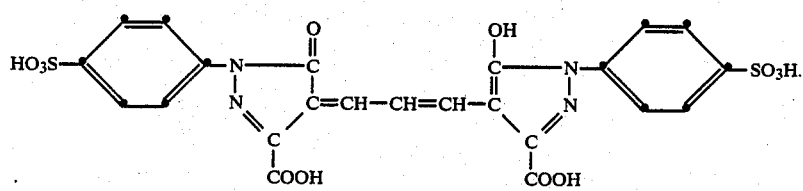

13. The element of claim 12 wherein said dye is:

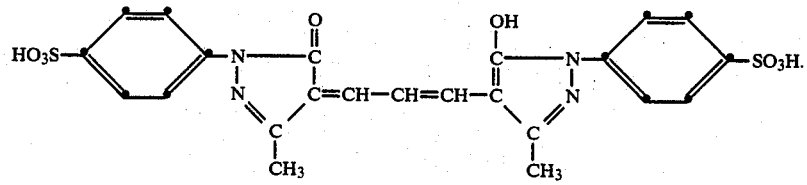

14. The element of claim 10 comprising a buffer which provides a pH in the range of from about 5 to about 11 under conditions of use.

15. A dry analytical element for the determination of albumin in a liquid sample,
said element comprising a support having thereon, in order and in fluid contact, a reagent zone and a spreading zone,
said reagent zone containing a dye having the structure:

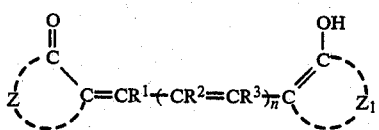

wherein n is zero or a positive integer up to 3; $R^1$, $R^2$ and $R^3$ are independently hydrogen, alkyl, cycloalkyl, aryl, alkoxy, aryloxy, hydroxy, carboxy, alkoxycarbonyl, amino or a nonaromatic heterocyclic group; and Z and $Z_1$ independently represent the carbon, nitrogen, oxygen or sulfur atoms needed to complete a 5- to 7-membered substituted or unsubstituted carbocyclic or heterocyclic ring.

16. The element of claim 15 wherein said dye is present in said reagent zone at a coverage of from about 0.01 to about 3 g/m².

17. A dry analytical element for the determination of albumin in a liquid sample,
said element comprising a support having thereon, in order and in fluid contact, a reagent layer and a spreading layer,
said reagent layer containing (1) a dye having the structure:

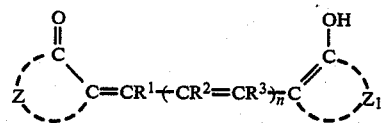

wherein n is zero or a positive integer up to 3; $R^1$, $R^2$ and $R^3$ are independently hydrogen, alkyl or aryl; and Z and $Z_1$ independently represent the carbon, nitrogen, oxygen or sulfur atoms needed to complete a substituted or unsubstituted 5- or 6-membered heterocyclic ring; and (2) a buffer providing a pH in the range of from about 6 to about 11 under conditions of use.

* * * * *